United States Patent [19]
Sahatjian

[11] Patent Number: 5,304,121
[45] Date of Patent: Apr. 19, 1994

[54] DRUG DELIVERY SYSTEM MAKING USE OF A HYDROGEL POLYMER COATING

[75] Inventor: Ronald Sahatjian, Lexington, Mass.

[73] Assignee: Boston Scientific Corporation, Watertown, Mass.

[21] Appl. No.: 795,976

[22] Filed: Nov. 22, 1991

Related U.S. Application Data

[63] Continuation-in-part of Ser. No. 635,732, Dec. 28, 1990, abandoned.

[51] Int. Cl.⁵ ............................................. A61M 31/00
[52] U.S. Cl. .................................... 604/53; 604/96; 604/265; 606/194
[58] Field of Search ............. 604/20, 53, 96, 99, 604/101, 265–266, 890.1, 892.1; 606/192, 194

[56] References Cited

U.S. PATENT DOCUMENTS

| | | |
|---|---|---|
| 4,026,296 | 5/1977 | Stoy et al. . |
| 4,299,226 | 11/1981 | Banka ........................... 604/53 X |
| 4,423,725 | 1/1984 | Baran et al. . |
| 4,481,323 | 11/1984 | Sterling . |
| 4,515,593 | 5/1985 | Norton . |
| 4,589,873 | 5/1986 | Schwartz et al. . |
| 4,603,152 | 7/1986 | Laurin et al. ................ 604/265 |
| 4,636,195 | 1/1987 | Wolinsky ........................ 604/53 |
| 4,693,243 | 9/1987 | Buras . |
| 4,714,460 | 12/1987 | Calderon ........................ 604/28 |
| 4,769,013 | 9/1988 | Lorenz et al. . |
| 4,784,647 | 11/1988 | Gross . |
| 4,923,450 | 5/1990 | Maeda et al. . |
| 4,950,256 | 8/1990 | Luther et al. ................. 604/265 |
| 5,026,607 | 6/1991 | Kiezulas ...................... 428/423.7 |
| 5,041,100 | 8/1991 | Rowland et al. ............. 604/265 |
| 5,087,244 | 2/1992 | Wolinsky et al. ............... 604/53 |
| 5,091,205 | 2/1992 | Fan . |
| 5,102,402 | 4/1992 | Dror et al. ................... 604/265 |
| 5,120,322 | 6/1992 | Davis et al. .................. 604/265 |
| 5,135,516 | 8/1992 | Sahatjian et al. . |
| 5,232,444 | 8/1993 | Just . |

FOREIGN PATENT DOCUMENTS

| | | |
|---|---|---|
| 0379156 | of 0000 | European Pat. Off. . |
| 0372088 | 6/1990 | European Pat. Off. . |
| 0399712 | 11/1990 | European Pat. Off. . |
| 380205 | 1/1924 | Fed. Rep. of Germany . |
| 1196327 | 7/1965 | Fed. Rep. of Germany . |
| 53-006430 | 1/1978 | Japan . |
| 0035036 | 10/1979 | Japan . |
| WO89/12478 | 12/1989 | PCT Int'l Appl. . |
| WO91/08790 | 6/1991 | PCT Int'l Appl. . |
| 1069826 | 1/1984 | U.S.S.R. . |
| 2112646 | 7/1983 | United Kingdom . |

OTHER PUBLICATIONS

Deutsch et al., "Low Stress Angioplasty at 60° C.: Attenuated Arterial Barotrauma", *Circulation* (Supp. III) 82:0281 (abstract) (Oct. 1990).

(List continued on next page.)

*Primary Examiner*—C. Fred Rosenbaum
*Assistant Examiner*—Corrine Maglione
*Attorney, Agent, or Firm*—Fish & Richardson

[57] ABSTRACT

The invention features a catheter and methods for delivering drug to tissue at a desired location of the wall of a body lumen. The catheter is constructed for insertion in a body lumen and has a catheter shaft and an expandable portion mounted on the catheter shaft. The expandable portion is expandable to a controlled pressure to fill the cross-section of the body lumen and press against the wall of the body lumen. In one embodiment, at least a portion of the exterior surface of the expandable portion is defined by a coating of a tenaciously adhered swellable hydrogel polymer. Incorporated in the hydrogel polymer is an aqueous solution of a preselected drug to be delivered to the tissue or plaque. The hydrogel polymer and drug are selected to allow rapid release of a desired dosage of the drug from the hydrogel polymer coating during compression of the hydrogel polymer coating against the wall of the lumen when the expandable portion is expanded. In other embodiments the polymer is released from the expandable portion in response to pressure, to coat the wall of the body lumen.

55 Claims, 4 Drawing Sheets

OTHER PUBLICATIONS

Wolinsky et al., "Local Introduction of Drugs into the Arterial Wall: A Percutaneous Catheter Technique", *J. Interventional Cardiol.* 2:219–228 (1989).

Chapman et al., "A Bioabsorbable Stent: Initial Experimental Results", *Circulation* (Supp III) 82:0283 (abstract) (Oct. 1990).

Guyton et al., "Inhibition of Rat Arterial Smooth Muscle Cell Proliferation by Heparin: In Vivo Studies with Anticoagulant and Nonanticoagulant Heparin," *Circ. Res.* 46:625–634 (May 1980).

Langer, "Drug Delivery," *IUPAC* Meeting, Montreal, Canada (Jul. 12, 1990).

McMath et al., "Experimental Application of Bioprotective Materials to Injured Arterial Surfaces with Laser Balloon Angioplasty", *Circulation* (Supp. III) 82:0282 (abstract) (Oct. 1990).

Thompson et al., "Heparin and Growth Control of Vascular Cells," *Ann. N.Y. Acad. Sci.* 556:255–267 (1989).

Tidd et al., "Comparison of Hydrophilic Polymer—Coated Latex, uncoated Latex and PVC Indwelling Balloon Catheters in the Prevention of Urinary Infection," *J. Urol.* 48:285–291 (1976).

Waller et al., "Vessel Wall Pathology After Angioplasty," *Cardio.* 57, 60, 69–72, 81 (Aug. 1990).

Waller et al., "Morphologic Observations Late after Coronary Balloon Angioplasty Mechanisms of Acute Injury and Relationship to Restenosis," *Radio.* 174:961–967 (Mar. 1990).

The Andreas Gruentzig Cardiovascular Center News Letter (Spring 1990).

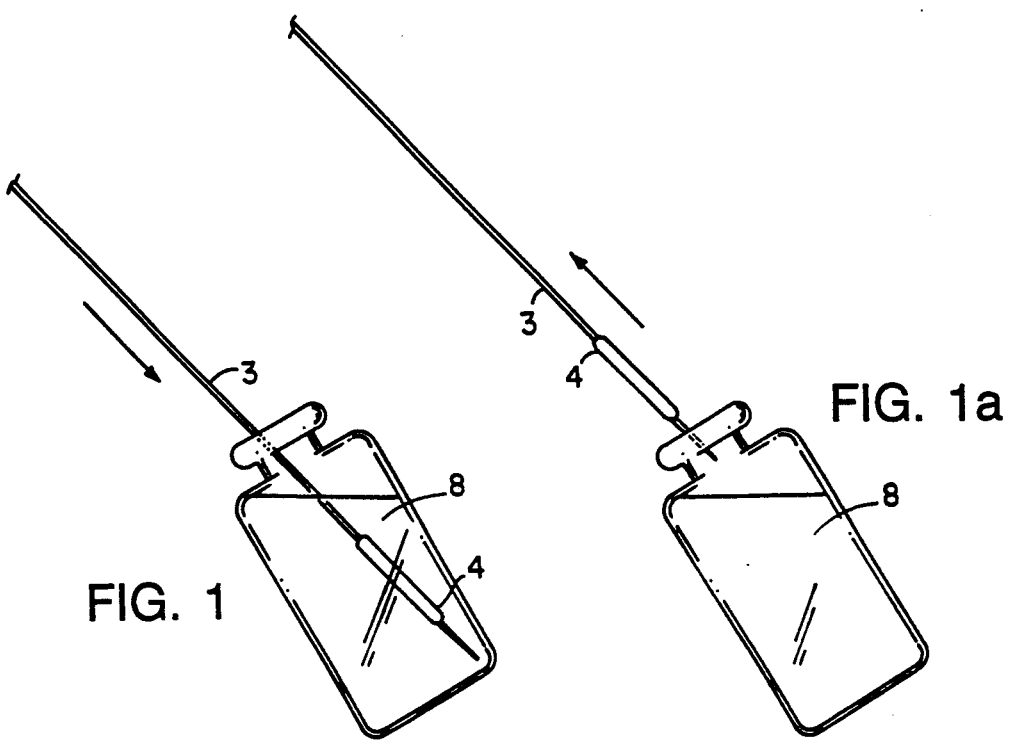
FIG. 1
FIG. 1a
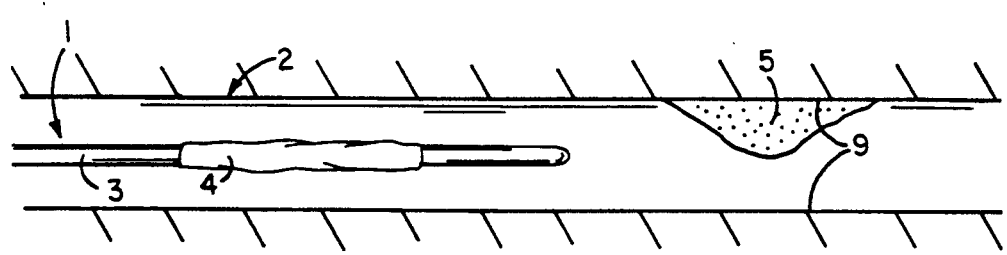
FIG. 1b
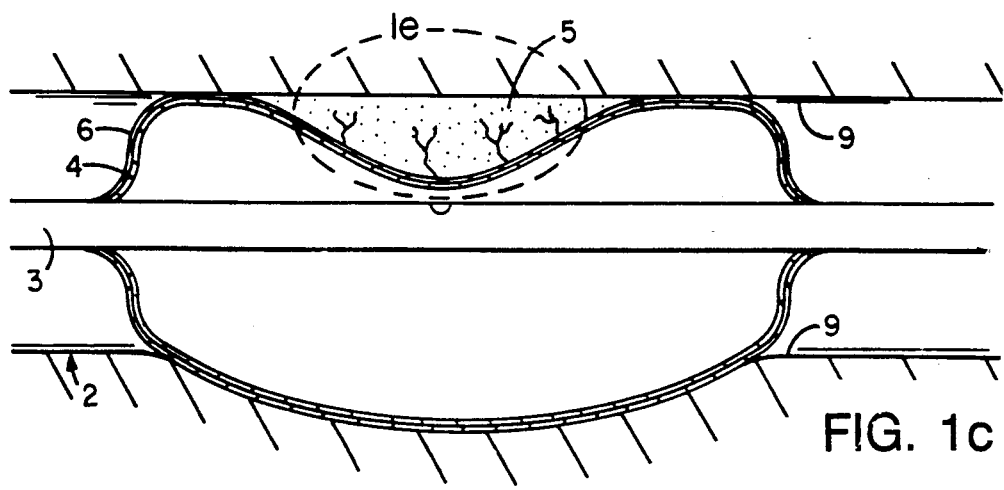
FIG. 1c

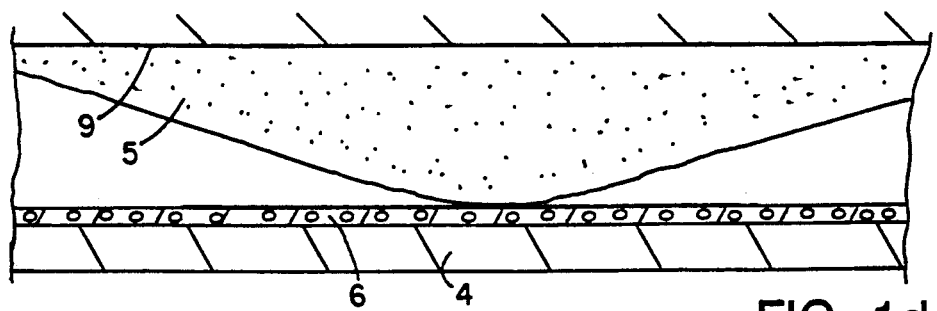
FIG. 1d
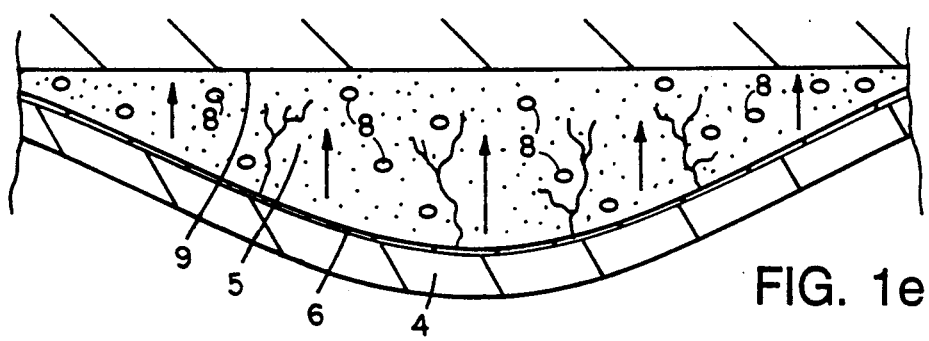
FIG. 1e
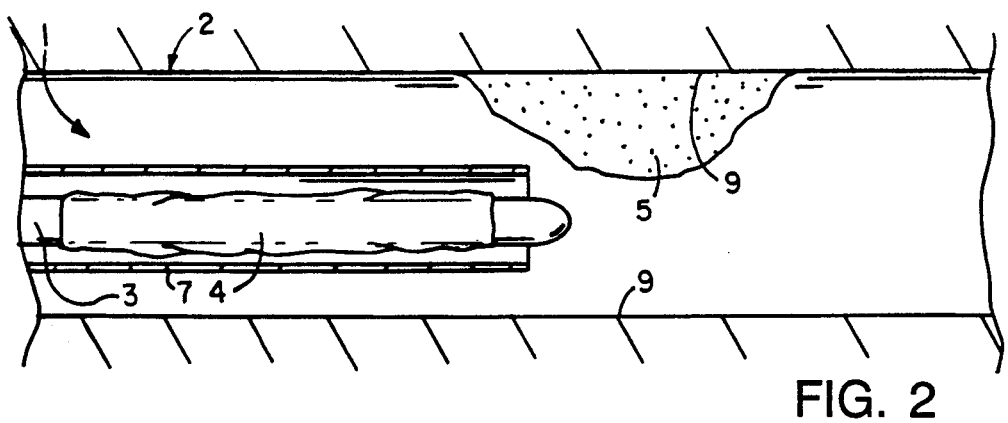
FIG. 2
FIG. 2a
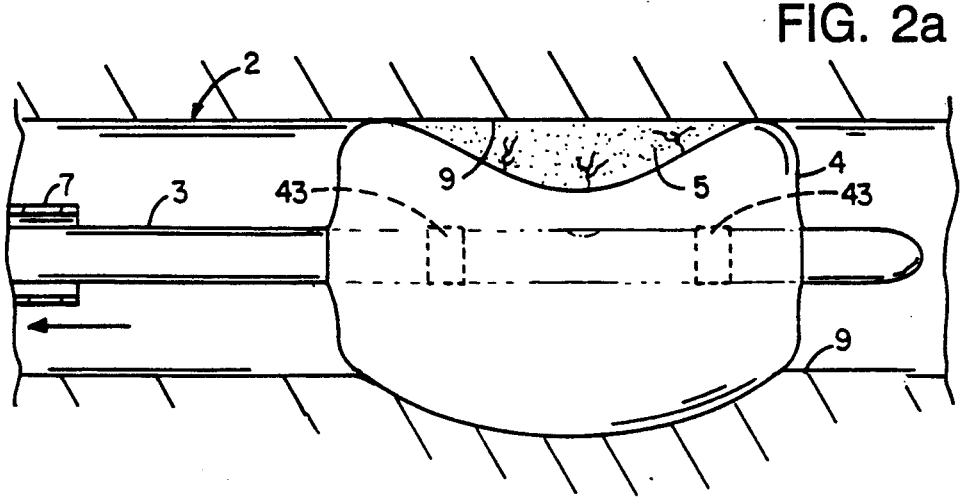

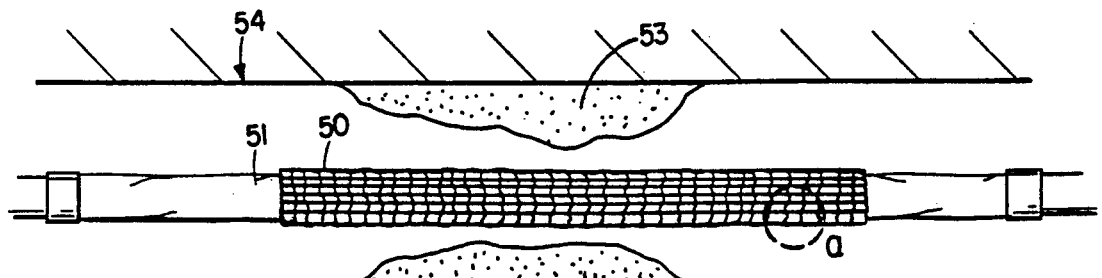
FIG. 4
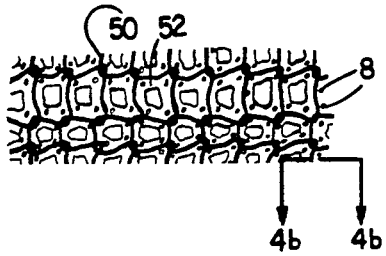
FIG. 4a
FIG. 4b
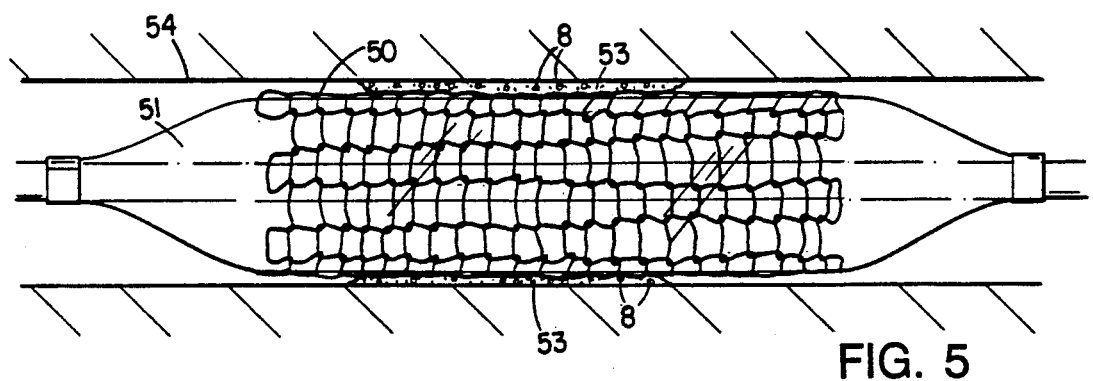
FIG. 5
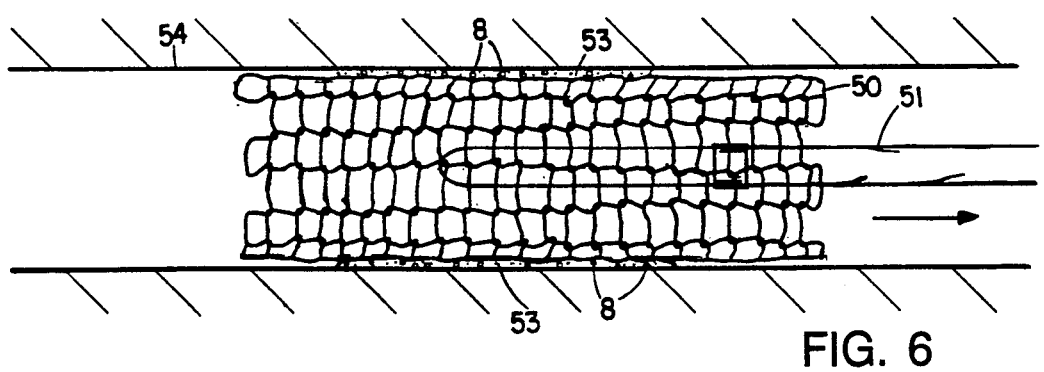
FIG. 6

DRUG DELIVERY SYSTEM MAKING USE OF A HYDROGEL POLYMER COATING

This application is a continuation-in-part of application U.S. Ser. No. 07/635,732, titled Balloon Drug Delivery System, filed Dec. 28, 1990 now abandoned. The entire contents of this application are hereby incorporated by reference.

This application is also a continuation-in-part of copending U.S. patent application Ser. No. 451,507 filed Dec. 15, 1989, now U.S. Pat. No. 5,135,516, issued Aug. 4, 1992.

FIELD OF THE INVENTION

The invention relates to delivery of drugs to the walls of body lumens.

BACKGROUND OF THE INVENTION

Systemic administration of drugs treats the organism as a whole, even though the disease may be localized, such as occlusion of a duct or vessel. Localization of a drug poses special problems in cases involving the walls of ducts and vessels, since, by nature, these organs serve as transport systems.

Arthrosclerotic disease, for example, causes localized occlusion of the blood vessels resulting from the build-up of plaque. As the deposits increase in size, they reduce the diameter of the arteries and impede blood circulation. Angioplasty, which involves the insertion of catheters, such as balloon catheters, through the occluded region of the blood vessel in order to expand it, has been used to treat arthrosclerosis.

The aftermath of angioplasty in many cases is problematic, due to restenosis, or closing of the vessel, that can occur from causes including mechanical abrasion and the proliferation of smooth muscle cells stimulated by the angioplasty treatment. Restenosis may also occur as a result of clot formation following angioplasty, due to injury to the vessel wall which triggers the natural clot-forming reactions of the blood.

SUMMARY OF THE INVENTION

In one aspect, the invention features a catheter and method for delivering drug to tissue at a desired location of the wall of a body lumen. The catheter is constructed for insertion in a body lumen and has a catheter shaft and an expandable portion mounted on the catheter shaft. The expandable portion is expandable to a controlled pressure to fill the cross-section of the body lumen and press against the wall of the body lumen. At least a portion of the exterior surface of the expandable portion is defined by a coating of a tenaciously adhered swellable hydrogel polymer. Incorporated in the hydrogel polymer is an aqueous solution of a preselected drug to be delivered to the tissue. The hydrogel polymer and drug are selected to allow rapid release of a desired dosage of the drug from the hydrogel polymer coating during compression of the hydrogel polymer coating against the wall of the lumen when the expandable portion is expanded.

Various embodiments may include one or more of the following features. The catheter is adapted for insertion in a blood vessel, and the expandable portion is an inflatable dilatation balloon adapted for inflation at pressures in the range for effecting widening of a stenosed blood vessel. The pressure is in the range of about 1 to 20 atmospheres. The hydrogel polymer and drug are effective to release about 20% or more of the drug during inflation in the pressure range. The compression is effective to deliver the drug over a duration of about 10 minutes or less. The hydrogel polymer coating is about 10 to 50 microns thick in the swelled, uncompressed state. The hydrogel polymer is selected from the group consisting of polycarboxylic acids, cellulosic polymers, gelatin, polyvinylpyrrolidone, maleic anhydride polymers, polyamides, polyvinyl alcohols, and polyethylene oxides. The hydrogel polymer is polyacrylic acid. The drug is an anti-thrombogenic drug selected from the group consisting of heparin, PPack, enoxaprin, aspirin and hirudin. The drug is an anti-proliferative drug selected from the group consisting of monoclonal antibodies, capable of blocking smooth muscle cell proliferation, heparin, angiopeptin and enoxaprin. The expandable portion is adapted for application of heat to the polymer material to control the rate of administration. The catheter further comprises a sheath member, extendable over the balloon to inhibit release of the drug into body fluids during placement of the catheter. The balloon catheter is a perfusion catheter having an expandable balloon. The expandable portion includes a stent, mountable in the blood vessel by expansion thereof. The drug is bound in the hydrogel polymer for slow time release of the drug after the compression of the hydrogel polymer by the expansion. The hydrogel polymer is a polyacrylic acid including an ammonium anion and the drug is heparin. The stent is expandable by a balloon. The catheter where the stent and balloon both include the swellable hydrogel coating incorporating the drug. The expandable portion is prepared by introducing an aqueous solution of the drug to the hydrogel polymer coating, the catheter is introduced to the body lumen to position the expandable portion at the point of desired drug application, and the expandable portion is expanded to enable delivery of the drug by compression of the hydrogel polymer coating against the wall at the body lumen. The expandable portion is positioned at a point of occlusion in the blood vessel and expanding the expandable portion at pressures sufficient to simultaneously dilate the vessel and deliver the drug by compression of the hydrogel polymer coating.

In a particular aspect, the invention includes a balloon catheter for delivering drug to tissue at a desired location of the wall of a blood vessel. The catheter is constructed for insertion in a blood vessel and has a catheter shaft and an expandable dilatation balloon mounted on the catheter shaft. The expandable balloon is expandable by an expansion controller to engage the tissue at a controlled pressure in the range of about 1 to 20 atmospheres to fill the cross-section of the blood vessel and press against the wall of the blood vessel. At least a portion of the exterior surface of the expandable balloon is defined by a coating of a tenaciously adhered swellable hydrogel polymer with a thickness in the range of about 10 to 50 microns in the swelled state, and incorporated within the hydrogel polymer coating, an aqueous solution of a preselected drug to be delivered to the tissue. The hydrogel polymer and drug are selected to allow rapid release of a desired dosage of about 20% or more of the drug solution from the hydrogel polymer coating during compression of the hydrogel polymer coating against the wall of the vessel when the expandable portion is expanded in the pressure range.

In various embodiments, the hydrogel polymer is selected from the group consisting of polycarboxylic acids, cellulosic polymers, gelatin, polyvinylpyrrolidone, maleic anhydride polymers, polyamides, polyvinyl alcohols, and polyethylene oxides. The hydrogel polymer is polyacrylic acid. The drug is an anti-thrombogenic drug selected from the group consisting of heparin, PPack enoxaprin, aspirin and hirudin. The drug is an anti-proliferative drug selected from the group consisting of monoclonal antibodies, capable of blocking smooth muscle cell proliferation, heparin, angiopeptin and enoxaprin. The catheter further comprises a sheath member, extendable over the balloon to inhibit release of the drug into body fluids during placement of the catheter.

In another aspect, the invention features a catheter for delivering drug to tissue at a desired location of the wall of a body lumen, comprising. The catheter is constructed for insertion in a body lumen having a catheter shaft and an expandable portion mounted on the catheter shaft, the expandable portion is expandable to a controlled pressure to fill the cross-section of the body lumen and press against the wall of the body lumen. At least a portion of the exterior surface of the expandable portion is defined by a coating of a body-fluid soluble polymer, and incorporated within the soluble polymer, a preselected drug to be delivered to the tissue. The soluble polymer and drug are selected to allow release of the polymer from the surface of the balloon during compression of the polymer coating against the wall of the body lumen when the expandable portion is expanded to coat the wall of the body lumen.

Various embodiments include the following. The polymer is selected from the group consisting of polycaprolactone, polyorthoesters, polylactic acids, polyglycolic acids, and albumin. The catheter where the drug is selected from anti-thrombogenic drugs and anti-proliferative drugs. The catheter where the expandable portion is adapted for application of heat to the polymer material to control the rate of administration. The catheter where the polymer is a meltable polymer, and the release of the polymer is aided by the application of heat.

In general, an advantage of the invention is the application of drugs by active diffusion directly into the tissue within the body requiring treatment. The drug is preferably applied in a rapid but low-stress, low energy manner that does not further injure the tissue to be treated, and administration is selectively and evenly distributed over the treated area such that the drug can be taken up by tissue and plaque, without, e.g., being washed away by body fluids.

DESCRIPTION OF PREFERRED EMBODIMENTS

We first briefly describe the drawings.

DRAWINGS

FIGS. 1-1a are enlarged views of a method of preparing an embodiment of the invention.

FIG. 1b is an enlarged cross-sectional view of an embodiment of the drug delivery balloon catheter of the invention being moved through a vessel toward an occlusion to be treated.

FIG. 1c is an enlarged cross-sectional view of the balloon in FIG. 1b, now fully inflated and at the site of occlusion.

FIG. 1d is a further enlarged, schematic cross-sectional view of the portion of FIG. 1c indicated in the circle 1e, but taken prior to full inflation.

FIG. 1e, which corresponds to the portion of FIG. 1c indicated in the circle 1e, is an enlarged, schematic cross-sectional view, as in FIG. 1d, but with the balloon under full inflation to release the drug coated on the balloon.

FIG. 2 is an enlarged cross-sectional view of another embodiment of the drug delivery balloon catheter of the invention including a sheath for covering the catheter as it is being moved through a vessel toward the occlusion to be treated.

FIG. 2a is an enlarged cross-sectional view of the catheter of FIG. 2 with the sheath retracted and balloon inflated at the site of occlusion.

Figure 3:
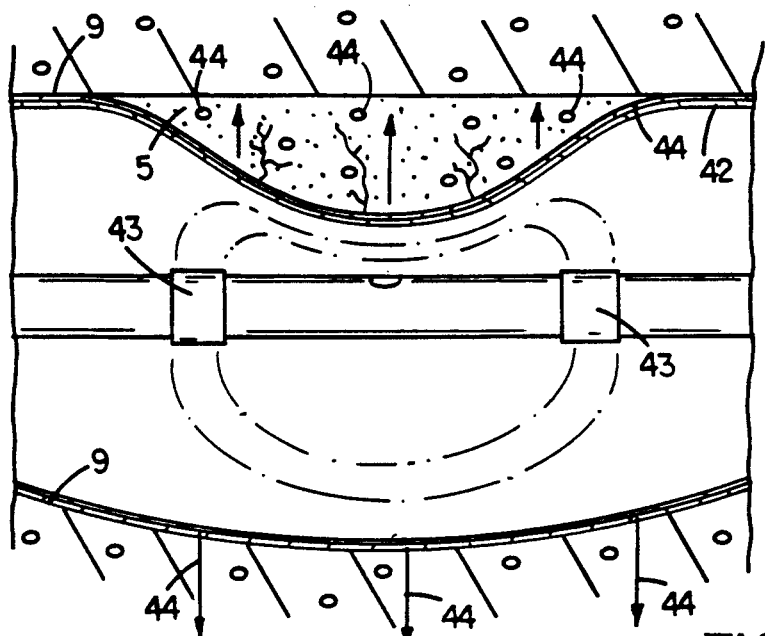

FIG. 3 is an enlarged, schematic cross-sectional view of another embodiment of the drug delivery balloon catheter in which the drug, originally held within a polymer applied to a thermal balloon of the invention, is now entering the surrounding tissue.

Figure 3A:
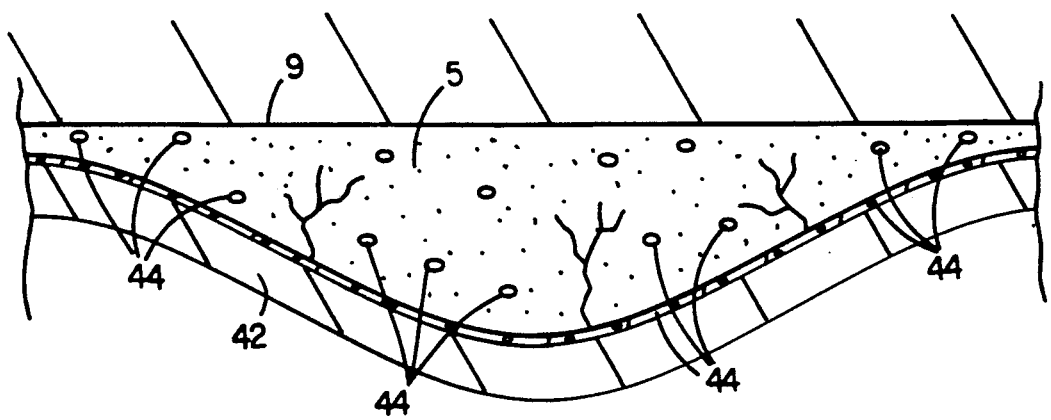

FIG. 3a is a further enlarged, schematic illustration of the embodiment of FIG. 3 and illustrates the entry of the drug, shown as circles, into the surrounding tissue.

FIG. 4 shows a balloon catheter with the hydrogel and drug coated endoprosthesis mounted on the balloon section, in the region of the thrombus, before radial expansion of the balloon section and endoprosthesis.

FIG. 4a is an enlargement of FIG. 4 showing the hydrogel polymer and drug coated endoprosthesis and FIG. 4b is a cross-section along the line b—b in FIG. 4a.

FIG. 5 shows the endoprosthesis compressed against the vessel wall by radial expansion of the balloon section with the drug diffused into the compressed thrombus before removal of the balloon catheter.

FIG. 6 shows the endoprosthesis positioned against the drug inside the compressed thrombus, after removal of the balloon catheter.

GENERAL DESCRIPTION

Referring to FIGS. 1-1e, in one embodiment, the invention includes a drug delivery balloon catheter device 1 comprising a catheter body 3 having a balloon 4 attached at its distal end. The balloon 4 on the catheter 3 includes a swellable hydrogel polymer coating 6. As shown in FIGS. 1-1a, a drug 8 in an aqueous solution is absorbed into the hydrogel with the balloon in the deflated state prior to insertion into the patient by the physician, e.g., the hydrogel-coated balloon may be immersed in a small tube or vial containing the drug. The drug may also be applied in the form of droplets, such as from an eyedropper, or the drug may be precipitated into the hydrogel prior to sterilization and sold as a finished device. Exposure of the hydrogel to the solution causes the hydrogel to swell.

As shown in FIG. 1b, typically the device 1 is inserted into the duct or vessel 2 having a region to be treated, such as an occlusion due to a deposition of plaque 5 on the vessel wall tissue 9. The device 1 is moved along the vessel to position the balloon 4 at the occlusion site, as shown in FIG. 1c. The vessel may be, for example, a narrow, tortuous opening through which the catheter is passed by torquing from the distal end. As the balloon is inflated the pressure created by the balloon against the tissue compresses the hydrogel and the drug is quickly and freely released for transfer by active diffusion into the plaque and tissue. The pressure applied to the plaque and tissue by the expansion of the balloon during application of the drug enhances transfer of the drug into the tissue and plaque. This process is referred to here as active diffusion. The balloon and catheter may be exposed to the body fluids of the lumen for a considerable time, e.g., up to about 15 minutes in some angioplasty procedures. An advantage of this invention is that large amounts of the drug, e.g., greater than 20%, even 30-50% or more, of the drug solution contained in the hydrogel, is diffused into the effected area in the short time duration which the hydrogel is compressed, e.g., 2-10 minutes after the balloon is inflated at the treatment site. The inflation pressure needed to dilate the vessel which also approximates the compression of the coating, is in the range of 1 to 20, typically about 2 to 10 atmospheres. The balloon is preferably a compliant material such as polyethylene which conforms to the shape of the lumen wall. The balloon may also be formed of other materials used in angioplasty, e.g., a nondistending material, such as polyethylene terephthalate (PET). Transporting the drug in the hydrogel prevents substantial release of the drug to body fluids prior to reaching the treatment area and during the drug application phase and allows large dosages to be delivered at a desired location.

In the embodiment of FIG. 1c, the balloon coating 6 is a swellable, compressible coating formed of the hydrogel and drug in solution. In FIG. 1d, the balloon 4 is shown inflated such that the coating 6, which has an initial thickness, is in contact with the occlusion 5 but not under substantial pressure. Further inflation of the balloon 4, as shown in FIG. 1e, compresses the hydrogel coating 6 against the occluded areas 5 causing quick release of the drug (represented by circles) contained in the coating 6 directly into the plaque and nearby healthy tissue, as indicated by the directional arrows, much in the nature of squeezing liquid from a sponge. The introduction of the drug into the plaque and tissue occurs simultaneously with widening of the occlusion by the dilatation balloon. Thus, as cracking of the plaque and stimulation of smooth muscle cells beneath the plaque and along healthy tissue of the vessel wall are caused by dilatation, a therapeutic drug is simultaneously applied to the effected area, e.g., to counteract the effects of the trauma. The thickness of the balloon 4 remains substantially the same, while the thickness of the coating 6 decreases due to the compression of the coating and the release of the drug 8. (FIGS. 1d-1e are schematic drawings and are not to scale with respect to the thickness of the balloon relative to the thickness of the hydrogel coating.) The drug carried by the balloon is evenly applied to plaque and tissue and isolated by the pressure of the balloon from the flow of body fluids in the lumen such that the drug, e.g., an anti-proliferative, may actively diffuse through the cracks formed in the plaque and reach the smooth muscle tissue. (It will also be understood that, as an alternative procedure, after dilation with a conventional angioplasty balloon catheter, a catheter carrying a drug-delivery, inflatable balloon, such as has been described, may be used to treat the vessel.)

The hydrogel coating is characterized by the ability to incorporate a substantial amount of the drug, typically in aqueous solution form, and is swellable such that the aqueous drug solution can be effectively squeezed out of the coating when pressure is applied by inflation of the balloon. Administration of the drug in this way enables the drug to be site specific, such that release of high concentrations and/or highly potent drugs may be limited to direct application to the diseased tissue. Furthermore, the drug is applied to the diseased tissue by the sponge-like coating in an even, gentle manner without disrupting or injuring the healthy tissue, while diffusion of the drug into the tissue is facilitated by the application of the pressure of the inflated balloon. The pressure also effectively forms a seal that prevents the flow of body fluids from washing the drug downstream of the treatment area. The dosage applied to the tissue may be controlled by regulating the time of presoaking the drug into the hydrogel coating to determine the amount of absorption of the drug solution by the hydrogel coating. Other factors affecting the dosage are the concentration of the drug in the solution applied to the coating and the releasability of the hydrogel coating, determined by, for example, the thickness of the hydrogel coating, its resiliency, porosity and the ability of the hydrogel coating to retain the drug, e.g., electrostatic binding or pore size, or the ionic strength of the coating, e.g., changed by changing the pH.

The drug may be an anti-thrombogenic drug, such as heparin or a heparin derivative, PPack (dextrophenylalanine proline arginine chloromethylketone) or an anti-proliferative, such as heparin (also known to have anti-proliferative properties), enoxaprin, angiopeptin, or monoclonal antibodies capable of blocking smooth muscle cell proliferation, or it may be hirudin or acetylsalicylic acid (i.e., aspirin). Dosages applied to the tissue, for example, of heparin are typically in the range of 10-30 mg of heparin solution containing 200-1,000 units of sodium heparin. For use with hydrogels, the drug is preferably water soluble, so that the drug may be easily absorbed into the coating matrix.

The sponge-like characteristics of the hydrogel allows the aqueous drug solution to be effectively squeezed out of the coating when pressure is applied by inflation of the balloon. The hydrogel and drug combination are preferably noncomplexed, i.e., held together through the ability of the hydrogel to swell and absorb the drug solution, thereby allowing the preferable free-release of the drug at the treatment site.

In particular embodiments it may be advantageous to select a hydrogel coating for a particular drug such that the drug is not substantially released into body fluids prior to application of pressure by expansion of the balloon. Binding of the drug may also be accomplished by electrostatic attraction of the drug to the coating or a coating additive or by mechanical binding, e.g., employing a coating having a pore size that inhibits inward flow of body fluids or outward flow of the drug itself, that might tend to release the drug. Hydrogels are particularly advantageous in that the drug is held within the hydrogen-bond matrix formed by the gel.

The hydrogel is a cross-linked polymer material formed from the combination of a colloid and water. Cross-linking reduces solubility and produces a jelly-like polymer that is characterized by the ability to swell and absorb a substantial amount of the drug, typically in aqueous solution form. The hydrogel coating is also particularly hydrophilic, water swellable, and lubricous (i.e., having a low coefficient of friction). Preferred hydrogels are polyacrylic acid polymers available as HYDROPLUS ® (Boston Scientific, Watertown, Mass.) and as described in U.S. Pat. No. 5,091,205, the portion disclosed in the parent application to this patent being incorporated by reference). The drug, e.g., heparin in aqueous solution, is absorbed into the coating without complexing and is freely released therefrom.

Such hydrogel-drug combinations deliver about half of the drug solution in response to pressures in the range of balloon angioplasty in the vascular system. In other particular embodiments, the hydrogel polymer includes acid groups and incorporates a drug which is anionic in nature that is bound by electrostatic attraction to cations in the coating, such as an ammonium cation, as described in "Lubricous Antithrombogenic Catheters, Guidewires, and Coatings" by Ronald Sahatjian et al, U.S. Pat. No,. 5,135,516, the entire contents of which are hereby incorporated by reference. The coating incorporating the quaternary ammonium salt is effective to deliver an initial fast release of drug during compression and a slow release of drug remaining in the compressed coating after compression and is particularly useful for coating vascular stents as described further below.

In general, when dry, the hydrogel coating is preferably on the order of about 1 to 10 microns thick, with a 2 to 5 micron coating typical. Very thin hydrogel coatings, e.g., of about 0.2-0.3 microns (dry) and much thicker hydrogel coatings, e.g., more than 10 microns (dry), are also possible. Typically, the hydrogel coating thickness may swell by about a factor of 6 to 10 or more when the hydrogel coating is hydrated. For example, a hydrogel coating of about 1 to 3 microns thickness, when dry, usually swells to about 10-30 microns thickness, when hydrated. Most preferably, the thickness of the coating is about 10 to 50 microns in the swelled, uncompressed state, and incorporates about 20-30 mg of drug solution.

Referring to FIG. 2, in another embodiment of a drug delivery balloon catheter, the catheter 3 is preferably very small in diameter and flexible, much in the nature of a guidewire, formed, in this case, of hollow tubing to which the coated balloon 4 is attached. The balloon is covered by a protective sheath 7 while the instrument I is inserted into the vessel or duct 2 and positioned at the treatment region. As the coated balloon 4 is positioned at the occluded site 5, (FIG. 2a) the protective sheath 7 is drawn back to expose the balloon 4. In an alternative embodiment, the sheath remains stationary while the guidewire-like catheter moves the coated balloon forward into the occluded region. The sheath 7 protects the coating and inhibits premature release of the drug. Such a sheath might be particularly advantageous with coatings and drugs without substantial chemical or mechanical binding. Additionally, the balloon catheter may be a thermal balloon catheter with electrodes 43, as more fully described below. The application of such heat may be employed to facilitate the release of the drug from the coating, to facilitate penetration of the drug into the tissue, or to facilitate the therapeutic action of the drug.

A procedure for preparing a drug delivery balloon with a hydrogel coating and an experiment of drug delivery for the above embodiments are presented in the following examples.

Examples

Example 1

A hydrogel coating on an angioplasty balloon may be formed as follows. The surface of the balloon (polyethylene) of an angiographic catheter is prepared by wiping down with clean cloth. The balloon has an O.D. (outer diameter) of about 3.5 mm (inflated). The balloon is coated with a solution of 4,4' diphenylmethane diisocyanate (MDI) in methylethylketone for 30 minutes. After drying in an air oven at 85° C. for 30 minutes, the balloon is dipped in a 1.7% solution of poly(acrylic acid) homopolymer having a molecular weight of about 3,000,000 in dimethylformamide (DMF) and tertiarybutyl alcohol. After drying at about 85° C. for 30 minutes, a smooth coating is obtained. The balloon is oven dried for 8 hours at 50° C. One function of the drying steps is to remove solvent from the coating. The surface of the balloon becomes instantly lubricous upon exposure to water. The polyisocyanate solution is at a concentration of about 0.5 to 10% by weight. The polyacrylic acid is at a concentration of about 0.1 to 10% by weight. The poly(carboxylic acid) to polyisocyanate molar ratio is generally about 1:1. The formation of the hydrogen is further described in U.S. Pat. No. 5,091,205 incorporated supra.

A solution of heparin salt may be applied to the coating. The solution is 10,000 units heparin sodium injection (Fisher Scientific, Pittsburgh, Pa.) USP Grade (1000 units/ml which is then added to 650 cc distilled water) and may be applied by dipping for, e.g., about 1 minute at room temperature. The heparin does not form a complex with the hydrogel solution and is freely released in response to compression of the polymer.

After a catheter is prepared for use as discussed above, the catheter may be introduced into the patient using the Seldinger technique and expanded at a desired location to compress the hydrogel and deliver the heparin solution.

Example 2

Delivery of a drug from a hydrogel coating on a balloon was investigated in the following experiment. Tritium-labeled Pebac was absorbed into a 3.5 mm Slider ® (balloon catheter from Boston Scientific Corporation) balloon coated with about a 40 micron thick (in the swelled state) coating as described in Example 1. The coating was dried and the radioactivity was counted. The balloon was then wetted with saline to swell the coating area. The balloon was inflated over a period of about one minute to about 4 atmospheres and held at this pressure for about 10 minutes in a thrombus created in an AV shunt from a baboon. The balloon was withdrawn and the amount of the drug in the thrombus was counted with a radiation counter. The experiment was performed with two different balloons using two different concentrations of PPack, balloon with 1-2 mg Pebac, and one balloon with 4 mg Pebac. Both balloons delivered about 50% of the Pebac into the thrombus.

Other Embodiments

Referring to FIG. 3, in another embodiment, the drug 44 is held within a polymer coating applied to the exterior of a thermal balloon, central wall portions 42 of which are shown in FIG. 3. The balloon is positioned in the lumen in the region to be treated and inflated such that the polymer coating is in contact with the tissue as shown in FIGS. 3-3a. Heating of the balloon 42 melts the polymer and releases the drug 44 in a gentle, even, low-energy manner into the affected tissue. Suitable polymers include, but are not limited to, albumin, and collagen, e.g., gelatin, such as gel foams, which typically melt between about 40°-60° C. or polyvinylpyrrolidone (PVP), which dissolves rapidly when heated. The thermal balloon typically operates between 40°-80° C. A suitable heated embodiment or that of FIG. 2a is discussed in Lennox et al., "Heated Balloon Catheters and the Like," U.S. Pat. No. 4,955,377, hereby incorporated by reference. Inflating liquid is heated as a result of $I^2R$ losses by radiofrequency current flowing in the inflation fluid, e.g., saline, between the electrodes 43 (see FIGS. 2a and 3), the liquid in turn heating the balloon wall. In the alternative, drugs which melt and which could be applied either with a meltable or non-meltable polymer binder might be used.

An advantage to the meltable coatings is that the polymer may be cross-linked, (e.g., by physical or chemical cross-linking) after application of the drug 44 to the balloon to inhibit release of the drug 44 as the balloon 42 is introduced through the body lumen to the area of treatment. The polymer itself typically does not melt off the balloon, but rather softens in a manner permitting release. However, in embodiments where the polymer is bioabsorbable, e.g., polycaprolactone, polyorthoesters, polylactic acids, and polyglycolic acids, some or even all of the polymer may dissolve off of the balloon.

The balloon may also be coated with a polymer incorporating a drug and inflated to press against the wall of the body lumen, where the polymer is selected to separate from the balloon and coat the wall of the lumen, in response to such pressure with or without the application of heat from the balloon. After application of the polymer, the balloon can be deflated and removed. In this embodiment, the polymer may be a blood soluble polymer such as albumin, collagen or the like, incorporating a drug such as heparin. The polymer produces a smooth coating on the wall of the lumen and releases the drug to the tissue over time as the polymer dissolves. Other soluble polymers are meltable and bioabsorbable polymers discussed above.

In another embodiment (see FIGS. 4–6) an endoprosthesis (stent) is used in combination with a balloon catheter drug delivery system. An endoprosthesis 50 is placed over the balloon catheter 51, and then coated with a noncomplexed hydrogel coating 52. The drug 8, shown as circles, in aqueous solution is then absorbed into the hydrogel coating 52. The balloon 51 and hydrogel and drug coated endoprosthesis 50 are slid until they reach the region of the occlusion 53 in the vessel 54. This is shown in FIG. 4. An enlargement of the drug and hydrogel polymer coated endoprosthesis 50 is shown in FIGS. 4a and 4b (thickness of coating 52 is greatly exaggerated). After the balloon 51 and hydrogel and drug coated endoprosthesis 50 have been positioned inside the vessel 54, the endoprosthesis 50 is radially expanded by the admission of pressure to the balloon 51 and compressed against the vessel wall 54 with the result that occlusion 53 is compressed, and the vessel wall 54 surrounding it undergoes a radial expansion. The pressure from inflating the balloon squeezes the hydrogel 52, freely releasing the drug 8 into the tissue. The endoprosthesis 50 is held in position in the expanded state as shown in FIG. 5. The pressure is then released from the balloon and the catheter is withdrawn from the vessel. FIG. 6 shows the drug 8 inside the compressed thrombus with the endoprosthesis expanded and left in position, with the balloon catheter being withdrawn from the lumen. It will be understood that only the endoprosthesis may include the hydrogel polymer coating. In the embodiments employing a hydrogel-coated stent, the hydrogel and drug are selected such that an initial high dosage of drug is delivered to adjacent tissue upon initial compression of the polymer and thereafter a slow, sustained time-release of drug remaining in the hydrogel polymer occurs. Preferred hydrogel-drug combinations are those that employ a binding of the drug, such as electrostatic binding, e.g., by using a polyacrylic acid hydrogel in combination with an ammonium cation and heparin. In this case, the coating continues to release drug after expansion of the stent and removal of the balloon catheter. The stent may be a balloon-expansible stent as described above or a self-expanding stent, e.g., of the type formed with super-elastic materials such as Nitinol.

Any of the embodiments discussed herein can be used with a protective sheath as described in FIGS. 2–2a. In addition, a heated balloon catheter may be used in all combinations of the embodiments above to enhance and control the rate of drug-solution delivery into tissue. Other compressible sponge-like polymers, e.g., non hydrogels which release drug solutions in response to pressure, might be used as described with respect to the embodiment of FIG. 1 et seq.

Still other embodiments are within the claims.

I claim:

1. A method for rapidly delivering a dose of a preselected aqueous-mobile drug into tissue or occlusive formation at a desired location of the wall of a vascular lumen, comprising:

providing a catheter constructed for insertion into a vascular lumen having a catheter shaft and an expandable portion mounted on said catheter shaft, said expandable portion being expandable in response to controlled inflation pressure to fill the cross-section of the vascular lumen and engage the tissue or occlusive formation of said vascular lumen, at least a portion of the exterior surface of the expandable portion being defined by a coating of a tenaciously adhered swellable hydrogel polymer, having said dose of said aqueous-mobile drug incorporated therein said hydrogel polymer selected to cause the coating to reach a characteristic swollen state of a thickness a number of times thicker than the thickness of the coating in its dry state as a result of absorption of aqueous fluid, and, when in said swollen state, said coating having characteristic compressibility, in response to compressive pressure within said expandable portion elevated above said inflation pressure, to squeeze the coating against said tissue or occlusive formation sufficiently to immediately, substantially, reduce the coating thickness, and force a substantial portion of said dose of said aqueous-mobile drug into said tissue or occlusive formation, preparing said expandable portion by introducing said drug to said hydrogen polymer coating, swelling said hydrogel polymer coating, positioning said expandable portion in said lumen at the point of desired drug application, expanding said expandable portion to cause immediate delivery of said drug by compression of said hydrogel polymer coating against the wall of said body lumen or said occlusive formation for a brief interval, during which said dose of said preselected drug is rapidly squeezed from said hydrogel coating and delivered to said tissue;

deflating said expandable portion, and removing said catheter from said body lumen.

2. The method of claim 1 further comprising introducing said catheter to an artery.

3. The method of claim 1 or 2 wherein said expandable portion is adapted for application of heat to said polymer material to control the rate of administration.

4. The method of claim 1 or 2 wherein said expandable portion includes a stent, placeable in said lumen by expansion thereof.

5. The method of claim 6 including a binding of said drug and said hydrogel polymer in a coating upon said stent for slow time release of drug remaining in said hydrogel polymer on said stent after compression of said hydrogel polymer by said expansion.

6. The method of claim 4 wherein said stent is balloon-expandable stent and said expandable portion is a stent positioned about said balloon.

7. The method of claim 6 wherein said stent and balloon both include said swellable hydrogel polymer coating incorporating said drug.

8. The method of claim 1 further comprising positioning said expandable portion at a point of occlusion in said vascular lumen and expanding said expandable portion at pressures sufficient to simultaneously dilate said vessel and deliver said drug by compression of said hydrogel polymer coating.

9. The method of claim 8 wherein said expandable portion is a dilatation balloon expandable to pressures in the range of about 1 to 20 atmospheres.

10. The method of claim 9 further comprising delivering about 20% or more of said drug during said compression.

11. The method of claim 10 wherein said drug is delivered in about ten minutes or less and the expandable portion is thereafter deflated.

12. The method of claim 11 wherein said hydrogel polymer is selected from the group consisting of polycarboxylic acids, cellulosic polymers, gelatin polyvinylpyrrolidone, maleic anhydride polymers, polyamides, polyvinyl alcohols, and polyethylene oxides.

13. The method of claim 12 wherein said hydrogel polymer is polyacrylic acid.

14. The method of any one of claims 1, 2, or 13 wherein said drug is an anti-thrombogenic drug selected from the group consisting of heparin, PPack enoxaprin, aspirin and hirudin.

15. The method of any one of claims 1, 2, or 13 wherein said drug is an anti-proliferative drug selected from the group consisting of monoclonal antibodies, capable of blocking smooth muscle cell proliferation, heparin, and enoxaprin.

16. A vascular catheter for rapidly delivering drug into tissue or occlusive formation at a desired location of the wall of a vascular lumen, effective to reduce blood clotting problems or proliferation of smooth muscle cells that may impede blood flow, comprising:

a catheter constructed for insertion into a vascular lumen having a catheter shaft and an expandable portion mounted on said catheter shaft, said expandable portion being expandable in response to controlled inflation pressure to fill the cross-section of the vascular lumen and engage the tissue or occlusive formation of said vascular lumen, at least a part of the exterior surface of the expandable portion being defined by a coating of a tenaciously adhered swellable hydrogel polymer, and incorporated within said hydrogel polymer, a preselected aqueous-mobile drug to be delivered to said tissue or occlusive formation, said drug selected from the groups of drugs that reduce vascular lumen occlusion problems caused by blood clots or tissue cell proliferation, said hydrogel polymer selected to cause the coating to reach a characteristic swollen state of a thickness a number of times thicker than the thickness of the coating in its dry state as a result of absorption of aqueous fluid, and, when in said swollen state, said coating having characteristic compressibility, in response t compressive pressure within said expandable portion elevated above said inflation pressure, to squeeze the coating against said tissue or occlusive formation sufficiently to immediately, substantially, reduce the coating thickness, and force a substantial portion of said aqueous-mobile drug into said tissue or occlusive formation, thereby to enable rapid administration of a desired dose of said drug into said tissue or occlusive formation.

17. The catheter of claim 16 wherein said catheter is a dilatation catheter sized, constructed and arranged for insertion in a stenosed vascular lumen, and said expandable portion is an inflatable dilatation balloon adapted for brief inflation at pressures in the range for effecting widening of said stenosed vascular lumen, said elevated compressive pressure being in a range effective to simultaneously cause, with said compression of said hydrogel a administration of said drug, widening of said vascular lumen.

18. The catheter of claims 17 or 16 wherein said hydrogel polymer is selected from the group consisting of polycarboxylic acids, cellulosic polymers, gelatin, polyvinylpyrrolidone, maleic anhydride polymers, polyamides, polyvinyl alcohols, and polyethylene oxides.

19. The catheter of claim 18 wherein said hydrogel polymer is polyacrylic acid.

20. The catheter of claim 17 or 16 wherein said drug is an anti-thrombogenic drug selected from the group consisting of heparin, PPACK, enoxaprin, aspirin and hirudin.

21. The catheter of claim 17 or 16 wherein said drug is an anti-proliferative drug selected from the group consisting of monoclonal antibodies, capable of blocking smooth muscle cell proliferation, heparin, angiopeptin and enoxaprin.

22. The catheter of claim 17 or 16 wherein said expandable portion is adapted for application of heat to said polymer material to control the rate of administration.

23. The catheter of claim 17 or 16 wherein said catheter further comprises a member, extending over said expandable portion to inhibit release of said drug into body fluids during placement of said catheter.

24. The catheter of claim 23 wherein said member is a retractable sheath.

25. The catheter of claim 17 or 16 wherein said expandable portion is constructed to withstand sufficient inflation pressure that application of said pressure to rapidly administer said drug simultaneously facilitates delivery of said drug into and through cracks in plaque formed by balloon angioplasty to reach smooth muscle tissue.

26. The catheter of claim 17 wherein said pressure 2 is in the pressure range of about 1 to 20 atmospheres.

27. The catheter of claim 17 or 26 wherein said hydrogel polymer is effective to release about 20% or more of said drug during inflation in said pressure range.

28. The catether of claims 17 or 26 wherein said expandable portion is constructed to withstand sufficient inflation pressure that application of said pressure to rapidly administer said drug simultaneously facilitates delivery of said drug into tissue or occlusive formation that lies deeper than the surface portion of the tissue or occlusive formation directly engaged by said expandable portion 29. The catheter of claim 28 wherein the response characteristic of said hydrogel to said compressive pressure is effective to deliver said dose of said drug over a duration of about 10 minutes or less.

30. The catheter of claim 28 wherein said hydrogel polymer coating is about 10 to 50 microns thick in the swelled, uncompressed state.

31. The catheter of claim 28 wherein said expandable portion includes a stent, placeable in said body lumen by expansion thereof.

32. The catheter of claim 28 wherein the hydrogel releases about 50% of the drug upon compression.

33. The catheter of claim 28 wherein the drug is precipitated into the hydrogel.

34. The catheter of claim 17 wherein said catheter is constructed as a perfusion catheter having an expandable balloon.

35. The catheter of any one of claims 16 wherein said expandable portion is constructed to withstand sufficient inflation pressure that application of said pressure to rapidly administer said drug simultaneously facilitates delivery of said drug into tissue or occlusive formation that lies deeper than the surface portion of the tissue or occlusive formation directly engaged by said expandable portion.

36. The catheter of claim 16 or 35 wherein said expandable portion includes a stent, placeable in said body lumen by expansion thereof.

37. The catheter of claim 36 including a binding of said drug and hydrogel polymer in a coating upon said stent for slow time release of drug remaining in said hydrogel polymer on said stent after said compression of said hydrogel polymer by said expansion.

38. The catheter of claim 37 wherein said hydrogel polymer coating on said stent is a polyacrylic acid including an ammonium anion, said drug is heparin and said binding is an electrostatic binding.

39. The catheter of claim 36 wherein said stent is a balloon-expandable stent and said expandable portion is a stent positioned about said balloon.

40. The catheter of claim 39 wherein said stent and balloon both include said swellable hydrogel coating incorporating said drug.

41. The catheter of claim 39 wherein said drug is an anti-thrombogenic drug selected from the group consisting of heparin, PPacK enoxaprin aspirin and hirudin.

42. The catheter of claim 39 wherein said drug is an anti-proliferative drug selected from the group consisting of monoclonal antibodies, capable of blocking smooth muscle cell proliferation, heparin, angiopeptin and enoxaprin.

43. The catheter of any one of claims 2, 16 or 35 wherein the response characteristic of said hydrogel to said compressive pressure is effective to deliver said dose of said drug over a duration of about 10 minutes or less.

44. The catheter of any one of claims 17, 16 or 35 wherein said hydrogel polymer coating is about 10 to 50 microns thick in the swelled, uncompressed state.

45. A vascular balloon catheter for rapidly delivering a dose of a preselected aqueous-mobile drug into tissue or occlusive formation at a desired location of the wall of a vascular lumen, comprising:

a catheter constructed for insertion into a vascular lumen having a catheter shaft and an expandable dilatation balloon mounted on said catheter shaft, said expandable balloon being expandable by an expansion controller to press against said tissue or occlusive formation at a compressive pressure in the range of about 1 to 20 atmospheres, said compressive pressure being elevated above the inflation pressure needed to fill the cross-section of the vascular lumen and engage the tissue or occlusive formation of said vascular lumen, at least a portion of the exterior surface of the expandable balloon being defined by a coating of a tenaciously adhered swellable hydrogel polymer having said dose of said aqueous-mobile drug incorporated therein, said hydrogel polymer selected to cause the coating to reach a characteristic swollen state of a thickness a number of times thicker than the thickness of the coating in its dry state as a result of absorption of aqueous fluid, and, when in said swollen state, said coating having characteristic compressibility, in response to said compressive pressure within said expandable balloon elevated above said inflation pressure, to squeeze the coating against said tissue or occlusive formation sufficiently to immediately, substantially, reduce the coating thickness, and force a substantial portion of said dose of said aqueous-mobile drug into said tissue or occlusive formation, said hydrogel polymer coating further characterized by having the capacity to incorporate a predetermined substantial amount of aqueous fluid and said drug and by being swellable by a factor of about 6 or more from a dried state to have a thickness in the range of about 10 to 50 microns in the swelled state, whereby rapid site specific release of a desired dose of about 20% or more of said aqueous-mobile drug from said hydrogel polymer coating is achieved during a brief interval of compression of said hydrogel polymer coating against the wall of the lumen when said expandable balloon is expanded in said pressure range.

46. The catheter of claim 45 wherein said hydrogel polymer is selected from the group consisting of polycarboxylic acids, cellulosic polymers, gelatin, polyvinylpyrrolidone, maleic anhydride polymers, polyamides, polyvinyl alcohols, and polyethylene oxides.

47. The catheter of claim 45 wherein said hydrogel polymer is polyacrylic acid.

48. The catheter of claim 39 wherein said catheter further comprises a sheath member, extendable over said balloon to inhibit release of said drug into body fluids during placement of said catheter.

49. The catheter of claim 45 wherein said drug is an anti-thrombogenic drug selected from the group consisting of heparin, Pebac, enoxaprin, aspirin and hirudin.

50. The catether of claim 45 wherein the drug is an anti-proliferative drug selected from the group consisting of monoclonal antibodies, capable of blocking smooth muscle cell proliferation, heparin, angiopeptin and enoxaprin.

51. The catheter of any one of claims 45, 16 or 35 or the method of claim 1 wherein the hydrogel releases about 50% of the drug upon compression.

52. The catheter or method of claim 51 wherein the polymer is polyacrylic acid.

53. The catheter of method of claim 52 wherein the drug is heparin.

54. The catheter or method of claim 50 wherein the hydrogel includes up to about 20-30 mg of aqueous drug solution.

55. The catheter of any one of claims 45, 16 or 35 or the method of claim 1 wherein the drug is precipitated into the hydrogel.

* * * * *

UNITED STATES PATENT AND TRADEMARK OFFICE
CERTIFICATE OF CORRECTION

PATENT NO. : 5,304,121

DATED : April 19, 1994

INVENTOR(S) : Ronald Sahatjian

It is certified that error appears in the above-identified patent and that said Letters Patent is hereby corrected as shown below:

Col. 4, line 59, "device I" should be --device 1--.

Col. 7, line 37, "instrument I" should be --instrument 1--.

Col. 8, line 67, after "heated" insert --balloon systems for this--.

Col. 11, line 7, claim 5, "claim 6" should be --claim 4--.

Col. 12, line 9, claim 16, "t" should be --to--.

Col. 12, line 63, claim 26, delete "2".

Col. 13, line 8, claim 28, after "portion" insert a period.

Col. 13, line 50, claim 40, "39" should be --6--.

Col. 13, line 55, claim 41, "PPacK" should be --PPACK--.

Col. 13, line 55, claim 41, after "enoxaprin" insert a comma.

UNITED STATES PATENT AND TRADEMARK OFFICE
CERTIFICATE OF CORRECTION

PATENT NO.   : 5,304,121

DATED        : April 19, 1994

INVENTOR(S)  : Ronald Sahatjian

It is certified that error appears in the above-identified patent and that said Letters Patent is hereby corrected as shown below:

Col. 13, line 61, claim 43, "2" should be --17--.

Col. 14, line 54, claim 48, "39" should be --45--.

Col. 14, line 60, claim 49, "Pebac" should be --PPACK--.

Col. 15, line 6, claim 54, "50" should be --53--.

Signed and Sealed this

Fourth Day of June, 1996

Attest:

BRUCE LEHMAN

*Attesting Officer*         Commissioner of Patents and Trademarks